(12) United States Patent
Kato et al.

(10) Patent No.: US 11,484,238 B2
(45) Date of Patent: Nov. 1, 2022

(54) GEL SHEET

(71) Applicant: SEKISUI PLASTICS CO., LTD., Osaka (JP)

(72) Inventors: Kazuki Kato, Ibaraki (JP); Ryo Iizuka, Ibaraki (JP); Yoshiki Nakayama, Tokyo (JP)

(73) Assignee: SEKISUI PLASTICS CO., LTD., Osaka (JP)

( * ) Notice: Subject to any disclaimer, the term of this patent is extended or adjusted under 35 U.S.C. 154(b) by 746 days.

(21) Appl. No.: 16/338,270

(22) PCT Filed: Sep. 22, 2017

(86) PCT No.: PCT/JP2017/034267
§ 371 (c)(1),
(2) Date: Mar. 29, 2019

(87) PCT Pub. No.: WO2018/062029
PCT Pub. Date: Apr. 5, 2018

(65) Prior Publication Data
US 2019/0313931 A1    Oct. 17, 2019

(30) Foreign Application Priority Data

Sep. 30, 2016  (JP) .............................. JP2016-193461
Mar. 6, 2017   (JP) .............................. JP2017-041815

(51) Int. Cl.
*A61B 5/00*     (2006.01)
*A61B 5/291*    (2021.01)
(Continued)

(52) U.S. Cl.
CPC ............ *A61B 5/291* (2021.01); *A61B 5/6833* (2013.01); *B32B 7/022* (2019.01); *B32B 27/08* (2013.01);
(Continued)

(58) Field of Classification Search
CPC ......... B32B 7/022; B32B 27/08; B32B 27/30; B32B 27/36; B32B 2307/50; C09J 7/10;
(Continued)

(56) References Cited

U.S. PATENT DOCUMENTS 6,038,464 A     3/2000  Axelgaard et al.
6,263,226 B1 *  7/2001  Axelgaard ........... A61N 1/0496
                                                 600/391
(Continued)

FOREIGN PATENT DOCUMENTS

JP      2-116408      9/1990
JP      2001-234129   8/2001
(Continued)

OTHER PUBLICATIONS

International Search Report issued in International Patent Application No. PCT/JP2017/034267, dated Dec. 12, 2017.
(Continued)

*Primary Examiner* — David Sample
*Assistant Examiner* — Donald M Flores, Jr.
(74) *Attorney, Agent, or Firm* — Greenblum & Bernstein, P.L.C.

(57) ABSTRACT

The present invention is intended to provide a gel sheet having a formulation providing an adhesive force on the skin side suitable for the skin (i.e., a gel having a low adhesive force and being able to withstand a tip pressure of a terminal and the like), and concurrently having a sufficient adhesive force against an electrode element on the side opposite to the skin side. The present invention is a gel sheet having a laminated structure of a layer A and a layer B, characterized in that the storage elastic modulus of the layer A at 23° C. and 10 Hz is 12,000 to 40,000 Pa, and the storage elastic modulus of the layer B at 23° C. and 10 Hz is 2,000 to 10,000 Pa.

7 Claims, 1 Drawing Sheet

(51) Int. Cl.
- *C09J 7/10* (2018.01)
- *B32B 27/08* (2006.01)
- *B32B 27/30* (2006.01)
- *B32B 27/36* (2006.01)
- *C09J 133/26* (2006.01)
- *C09J 11/08* (2006.01)
- *C09J 7/30* (2018.01)
- *B32B 7/022* (2019.01)
- *A61B 5/259* (2021.01)
- *A61L 15/24* (2006.01)

(52) U.S. Cl.
CPC .............. *B32B 27/30* (2013.01); *B32B 27/36* (2013.01); *C09J 7/10* (2018.01); *C09J 7/30* (2018.01); *C09J 11/08* (2013.01); *C09J 133/26* (2013.01); *A61B 5/259* (2021.01); *A61B 2562/14* (2013.01); *A61L 15/24* (2013.01); *B32B 2307/50* (2013.01); *C09J 2301/208* (2020.08); *C09J 2301/312* (2020.08); *C09J 2429/00* (2013.01); *Y10T 428/24942* (2015.01)

(58) Field of Classification Search
CPC ... C09J 7/30; C09J 11/08; C09J 133/26; C09J 2301/208; C09J 2301/312; C09J 2429/00; Y10T 428/24942
See application file for complete search history.

(56) References Cited

U.S. PATENT DOCUMENTS

| | | |
|---|---|---|
| 2011/0033699 A1 | 2/2011 | Hayashi et al. |
| 2015/0238106 A1 | 8/2015 | Lappalainen et al. |

FOREIGN PATENT DOCUMENTS

| | | |
|---|---|---|
| JP | 2002-501804 | 1/2002 |
| JP | 2005-213455 | 8/2005 |
| JP | 2006-55268 | 3/2006 |
| JP | 2012-200348 | 10/2012 |
| JP | 2013-18242 | 1/2013 |
| JP | 2015-59184 | 3/2015 |
| JP | 2016-501049 | 1/2016 |
| KR | 2011-0010068 | 1/2011 |

OTHER PUBLICATIONS

International Preliminary Report on Patentability issued with respect to Patent Application No. PCT/JP2017/034267, dated Apr. 2, 2019.
European Search Report, European Patent Office, Application No. 17855983.7, dated Apr. 3, 2020.
Korean Office Action, Korean Patent Office, Application No. 10-2019-7005548, dated Jun. 10, 2020.

* cited by examiner

GEL SHEET

TECHNICAL FIELD

The present invention relates to a gel sheet. In particular, the present invention relates to an adhesive gel sheet for skin for bioelectrode, medical tape and the like used for electroencephalography or rehabilitation of the elderly for which it is necessary to reduce damage to the skin.

BACKGROUND ART

The gel sheet is preferably used as a surgical tape to be attached to a living body, a fixing tape for various medical devices, a bioelectrode pad to be attached to a living body, an electrode for an electrocardiogram, an industrial adhesive tape for a building material and an electronic material and the like. Properties required for a gel sheet are different depending on the respective uses.

For example, a fixing tape is required to be firmly fixed to the skin, and to reduce sweating and rash when attached to the skin or damage when peeling off the tape. Further, since a bioelectrode pad is attached to the skin for a long time, it is necessary to keep an adhesive force on the electrode element side, in addition to adhesion to the skin.

Along with the recent aging of the population, there is a demand for medical electrodes (for electroencephalography or for stimulating the muscles for rehabilitation) that are simpler and more accurate in measurements. For example, in electroencephalography, cellulose fibers containing physiological saline were conventionally used as an electrode. However, since cellulose fibers have poor water retention, there were problems of change in moisture content over time and in handling at the time of measurements.

Therefore, in Patent Literature 1 and the like, it is proposed to use a hydrogel for taking an electrocardiogram. However, since a gel material is inherently designed to attach to the skin, it is soft and adhesive. Therefore, when setting an electrode on the scalp, there was a problem in that the hair may get entangled with the adhesive medium. Further, since the gel material follows the fine irregularities of the skin, there was a problem in that damage was incurred to the skin when peeling off the gel. Moreover, since the hydrogel is a very soft material, there is a possibility that the hydrogel may break by the pushing pressure of the convex portion of the electrode in making measurements by point contact such as electroencephalography.

CITATION LIST

Patent Literature

Patent Literature 1: JP Patent Publication (Kohyo) No. 2016-501049 A

SUMMARY OF INVENTION

Technical Problem

The present invention, in view of the conventional circumstances mentioned above, is intended to provide a gel sheet having a formulation providing an adhesive force on the skin side suitable for the skin (i.e., a gel having a low adhesive force and being able to withstand a tip pressure of a terminal and the like), and concurrently having a sufficient adhesive force against an electrode element on the side opposite to the skin side.

Solution to Problem

As a result of intensive investigation, the inventors of the present invention have found that a gel sheet having adhesion and repulsion incurring minor damage to a delicate skin can be obtained by laminating gels having different compositions, imparting different theological properties to a layer attached to the skin and a layer on the opposite side, and making the layer attached to the skin harder than the layer on the opposite side, and completed the invention. In other words, the summary of the present invention is as follows.

(1) A gel sheet having a laminated structure of a layer A and a layer B, wherein a storage elastic modulus of the layer A at 23° C. and 10 Hz is 12,000 to 40,000 Pa, and a storage elastic modulus of the layer B at 23° C. and 10 Hz is 2,000 to 10,000 Pa.

(2) The gel sheet according to (1), wherein an adhesive force of the layer A to a Bakelite plate is 0.1 to 2.0 N/20 mm, and an adhesive force of the layer B to the Bakelite plate is 2.5 to 15 N/20 mm, (3) The gel sheet according to (1) or (2), having a thickness of 0.2 mm to 2.0 mm.

(4) The gel sheet according to any one of (1) to (3), wherein a ratio of a thickness of the layer A to a thickness of the layer B (A/B) is 0.25 to 3.5.

(5) The gel sheet according to any one of (1) to (4), wherein the layer A and the layer B are hydrogels comprising a polymer matrix, water and polyhydric alcohol, and the polymer matrix is a copolymer of one or more monofunctional monomers selected from a (meth)acrylamide-based monomer and (meth)acrylate ester, and a crosslinkable monomer.

(6) The gel sheet according to (5), wherein the layer A further comprises polyvinyl alcohol.

(7) The gel sheet according to any one of (1) to (6), wherein an alternating current impedance of the layer A and that of the layer B at 10 Hz are both 1,000Ω or less.

(8) The gel sheet according to any one of (1) to (7), being an adhesive gel sheet for skin to be used by attaching a surface of the layer A to the skin.

The present specification contains the disclosure of JP Patent Application Nos. 2016-193461 and 2017-041815, which are the basis of priority of the present application.

Advantageous Effects of Invention

According to the present invention, by constituting a gel sheet by more than one layer and making a storage elastic modulus of a layer attached to the skin higher to form a hard layer and a soft layer, it is possible to exert hardness (repulsion and durability) and adhesive force depending on the respective adherends of the skin and an electrode element, and to preferably use the gel sheet in applications such as pressing and fixing a convex portion of an electrode to a scalp via the gel sheet without having hair entangled, as an electrode used for electroencephalography and the like.

DESCRIPTION OF EMBODIMENT

The present invention is described in detail hereinafter.

Figure 1:
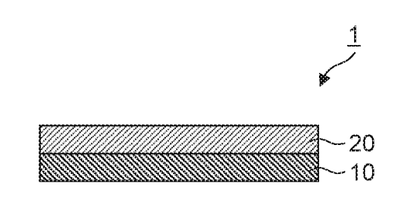
FIG. 1 is a view schematically showing a cross-sectional view of an embodiment of a gel sheet according to the present invention.

FIG. 1 shows a cross-sectional view of one embodiment of a gel sheet according to the present invention. A gel sheet 1 according to the embodiment is constituted by laminating a layer A 10 and a layer B 20. Further, the storage elastic modulus of the layer A 10 at 23° C. and 10 Hz is 12,000 to 40,000 Pa, and the storage elastic modulus of the layer B 20 at 23° C. and 10 Hz is 2,000 to 10,000 Pa.

The gel sheet 1 is preferably used as a bioelectrode, the layer A 10 is attached to a skin, and the surface of the layer B 20 is brought into contact with an electrode element. Since the layer A 10 is harder than the layer B 20 and the layer B is softer, the layer B 20 adheres well to the electrode element and no air bubbles are developed between the layer B and the electrode element.

Moreover, it is preferable that the adhesive force of the layer A 10 to a Bakelite plate be 0.1 to 2.0 N/20 mm, and the adhesive force of the layer B 20 to the Bakelite plate be 2.5 to 15 N/20 mm. For the layer B 20, it is particularly preferably 2.5 to 8.0 N/20 mm. Since the adhesive force of the layer A is small, damage is not incurred when peeling off the gel sheet from the skin and hair is not tangled. When adopting a constitution that the layer B side is not removed from the electrode element, it is desirable that the adhesive force of the layer B be high.

Further, in the present invention, the adhesive force to the Bakelite plate means the average value of measured stress values of 3 tests (total of 15 points) performed in accordance with JIS Z0237: 2009 as follows: a gel sheet is cut into 120 mm×20 mm, and a Bakelite plate is attached on the side of either the layer A or the layer B to be measured; test pieces are prepared by rolling a pressure roller of 2 kg back and forth once; and stress values (N/20 mm) are measured using a rheometer (CR-500DX, manufactured by Sun Scientific Co., Ltd.), under the measuring conditions of an angle of 90° and a speed of 300 mm/min at points from the starting point of measurement to predetermined peeling points (30, 40, 50, 60, and 70 mm). The measurements shall be performed in an environment of a temperature of 23±5° C. and a humidity of 55%±10%.

It is necessary that the layer A 10 and the layer B 20 have adhesion and shock-absorbing properties (repulsive force), and in the case of using the gel sheet as a bioelectrode, it is preferable to further have electric conductivity. In particular, it is preferable that the layer A 10 and the layer B 20 be constituted of a hydrogel containing water in view of its application to human body. The hydrogel is excellent in water retention and the like, and is used in a variety of fields such as medical care, pharmaceuticals, food products, civil engineering, bioengineering, sports, and the like.

As the hydrogel, for example, a hydrogel containing a polymer matrix, water, and polyhydric alcohol is preferably used.

As an example, the polymer matrix can be formed of a copolymer of a monofunctional monomer having one ethylenically unsaturated group and a crosslinkable monomer, but it is not limited thereto.

As the monofunctional monomer, a water-soluble monomer such as (meth)acrylamide-based monomer or (meth)acrylate ester is preferably used.

Specific examples of the (meth)acrylamide-based monomer include N,N-dialkyl(meth)acrylamide such as (meth)acrylamide, N,N-dimethyl(meth)acrylamide and N,N-diethyl(meth)acrylamide; N-alkyl(meth)acrylamide such as N-isopropyl(meth)acrylamide, N-methyl(meth)acrylamide, N-ethyl(meth)acrylamide and N-propyl(meth)acrylamide; N-hydroxyalkyl(meth)acrylamide such as N-hydroxyethyl (meth)acrylamide and N-hydroxymethyl(meth)acrylamide; N-alkoxyalkyl(meth)acrylamide such as N-ethoxymethyl (meth)acrylamide, N-propoxymethyl(meth)acrylamide, N-butoxymethyl(meth)acrylamide, N-isobutoxymethyl (meth)acrylamide, N-pentoxymethyl(meth)acrylamide, N-hexyloxymethyl(meth)acrylamide, N-heptoxymethyl (meth)acrylamide, N-octoxymethyl(meth)acrylamide, N-ethoxyethyl(meth)acrylamide, N-propoxyethyl(meth) acrylamide, and N-butoxyethyl(meth)acrylamide; a cationic acrylamide-based compound containing an amino group such as dimethylaminopropyl(meth)acrylamide; an anionic monofunctional monomer containing a sulfonic acid group such as 4-acryloyl morpholine, and tert-butyl acrylamide sulfonic acid, or a salt thereof; derivatives thereof; and the like. Among the above, at least one selected from the group consisting of (meth)acrylamide, N,N-dimethyl(meth)acrylamide, N,N-diethyl(meth)acrylamide, N-isopropyl(meth) acrylamide, N-methyl(meth)acrylamide, N-ethyl(meth) acrylamide, N-propyl(meth)acrylamide, N-hydroxyethyl (meth)acrylamide, N-hydroxymethyl(meth)acrylamide, dimethylaminopropyl(meth)acrylamide, 4-acryloyl morpholine, tert-butyl acrylamide sulfonic acid, and salts thereof is preferably used, but is not limited thereto.

Specific examples of the (meth)acrylate ester include, (meth)acrylate alkyl ester with the alkyl group containing 1 to 18 carbon atoms, for example, (meth)acrylate alkyl ester such as methyl (meth)acrylate, ethyl (meth)acrylate, n-propyl (meth)acrylate, isopropyl (meth)acrylate, n-butyl (meth) acrylate, isobutyl (meth)acrylate, tert-butyl (meth)acrylate, n-hexyl (meth)acrylate, n-octyl (meth)acrylate, isooctyl (meth)acrylate, 2-ethylhexyl (meth)acrylate, n-nonyl (meth) acrylate, isononyl (meth)acrylate, n-pentyl (meth)acrylate, n-decyl (meth)acrylate, isodecyl (meth)acrylate, n-lauryl (meth)acrylate, tridecyl (meth)acrylate, and n-stearyl (meth) acrylate; alicyclic (meth)acrylate such as cyclohexyl (meth) acrylate, isobornyl (meth)acrylate, and 1-adamantyl (meth) acrylate; alkoxy group-containing (meth)acrylate ester such as methoxy polyethylene glycol(meth)acrylate such as 2-methoxyethyl (meth)acrylate, ethoxyethoxyethyl(meth) acrylate, and methoxytriethylene glycol(meth)acrylate; hydroxyalkyl (meth)acrylate (where an aryl group may be bonded to a hydroxyalkyl group via an ether bond) such as 2-hydroxyethyl (meth)acrylate, 2-hydroxypropyl (meth) acrylate, 2-hydroxy-3-phenoxypropyl (meth)acrylate, and 2-hydroxybutyl (meth)acrylate; glycerin mono(meth)acrylate; polyalkylene glycol mono(meth)acrylate such as polyethylene glycol mono(meth)acrylate and polyethylene glycol-polypropylene glycol copolymer; (meth)acrylate ester having an aromatic ring such as benzyl (meth)acrylate; (meth)acrylate ester having a heterocyclic ring such as tetrahydrofurfuryl (meth)acrylate; and the like.

In addition to the (meth)acrylamide-based monomers mentioned above, as required, the monofunctional monomer mentioned above may be (meth)acrylate or a salt thereof, (meth)acrylate ester, a vinyl amide-based monofunctional monomer such as vinyl pyrrolidone, vinyl acetamide, vinyl formamide; a nonionic monofunctional monomer such as allyl alcohol, and a styrene-based monomer, and the like. These monofunctional monomers may be used singly or in combinations of two or more. Further, in the present specification, (meth)acryl means acryl or methacryl, and (meth) acrylate means acrylate or methacrylate.

The content of the structural unit derived from the monofunctional monomer mentioned above in each of the layer A and the layer B is not particularly limited, but it is preferably in the range of 10 to 30% by weight and more preferably in the range of 15 to 25% by weight with respect to the total amount of the hydrogel. When the content of the structural unit derived from the monofunctional monomer mentioned above is too small, the shape retaining property of the hydrogel becomes insufficient and there is a possibility that it is too soft or easily torn apart. Moreover, when the content of the structural unit derived from the monofunctional monomer mentioned above is too large, it will not be dissolved from the perspective of solubility in water, and therefore it is appropriately determined in view of balancing these aspects. As required, the content of the monofunctional monomer in the layer A may be increased, and the gel may be hardened so that the storage elastic modulus of the layer A becomes 12,000 to 40,000 Pa.

As the crosslinkable monomer mentioned above, it is preferable to use a monomer having two or more polymerizable double bonds in the molecule. Specific examples thereof include polyfunctional (meth)acrylamide or (meth)acrylate such as N,N'-methylenebis(meth)acrylamide, N,N'-ethylenebis(meth)acrylamide, (poly)ethylene glycol di(meth)acrylate, (poly)propylene glycol di(meth)acrylate, glycerin di(meth)acrylate and glycerin tri(meth)acrylate, tetraallyloxyethane; diallyl ammonium chloride; and the like, and these may be used singly or in combinations of two or more. Further, as the crosslinkable monomer having two or more polymerizable double bonds in the molecule mentioned above, a polyglycerol derivative which is a polyfunctional compound having two or more (meth)acryloyl groups or vinyl groups and having a molecular weight of 400 or more as described in JP Patent No. 2803886 can also be used.

The amount of the crosslinkable monomer to be added is preferably in the range of 0.01% by weight to 0.1% by weight with respect to the total amount of the hydrogel. When the amount to be added is too small, the crosslinking density becomes low, the shape stability becomes poor, and at the same time the cohesive force decreases, the holding force of the gel material itself decreases, and handling of the gel becomes difficult. Moreover, since a portion of the gel material remains on an adherend when peeling off, handling property of the gel sheet deteriorates. Moreover, when the amount of the crosslinkable monomer to be added is too large, the adhesive force becomes small and there is a possibility that the gel becomes hard and brittle.

Moreover, the content of water in the hydrogel is not particularly limited, but it is preferably 10 to 60% by weight, and more preferably 15 to 30% by weight, with respect to the total amount of the hydrogel. When the content of water is too small, the water content of the hydrogel with respect to the equilibrium water content decreases, the hygroscopicity of the hydrogel becomes large, and the hydrogel may degenerate (for example, swell) over time. Moreover, When the content of water is too large, the water content of the hydrogel with respect to the equilibrium water content increases, contraction and property changes of the hydrogel may develop from drying.

Examples of the polyhydric alcohol are not particularly limited, and the examples include diols such as ethylene glycol, triethylene glycol, 1,6-hexanediol, 1,9-nonanediol, propylene glycol, and butanediol; a 3-valent or higher polyhydric alcohol such as glycerin, pentaerythritol, sorbitol; a polyhydric alcohol condensate such as polyethylene glycol, polypropylene glycol and polyglycerin; a modified polyhydric alcohol such as polyoxyethylene glycerin; and the like.

Among the polyhydric alcohols, it is preferable to use a polyhydric alcohol that is in a liquid state in the working temperature range of the hydrogel (for example, around 20° C. when used indoors), specifically, ethylene glycol, triethylene glycol, propylene glycol, polypropylene glycol, polyethylene glycol, polyglycerin, glycerin and the like are preferable.

The content of the polyhydric alcohol in the hydrogel is not particularly limited, but it is preferably in the range of 20 to 70% by weight, and more preferably in the range of 25 to 65% by weight, with respect to the total amount of the hydrogel. When the content of the polyhydric alcohol is too small, moisture retention and plasticity of the obtained hydrogel are poor, transpiration of moisture becomes remarkable, and stability of the hydrogel over time as well as flexibility lack, and therefore sufficient adhesion may not be obtained. When the content of the polyhydric alcohol is too large, the amount of the polyhydric alcohol exceeds the amount of polyhydric alcohol that the polymer matrix can retain, and the physical properties of the hydrogel change due to bleed-out of the polyhydric alcohol from the surface of the hydrogel, and sufficient adhesion may not be obtained. Therefore, the content of the polyhydric alcohol is appropriately determined in view of balancing these aspects.

In particular, with respect to the layer A 10, in order to have a buffer action while maintaining the flexibility of the gel, it is possible to provide a S-IPN (Semi-Interpenetrating Polymer Network) structure to the skeleton by mixing a water-soluble synthetic polymer such as polyvinyl alcohol at the time of polymerization. By containing a water-soluble synthetic polymer such as polyvinyl alcohol, the storage elastic modulus of the layer A is increased and the gel can be hardened.

When polyvinyl alcohol is contained in the layer A, and if the degree of polymerization of the polyvinyl alcohol is too small, the effect of improving the mechanical strength cannot be obtained. Conversely, if the degree of polymerization is too large, the viscosity increase is significant and a homogeneous mixture cannot be prepared when dissolving the polyvinyl alcohol in a monomer containing solution prepared at the time of making the gel. Therefore, the degree of polymerization is appropriately determined in view of balancing these aspects. Preferably, the viscosity average degree of polymerization is 500 to 3,000.

Moreover, when the degree of saponification of the polyvinyl alcohol used in the present embodiment is too small, the solubility at the time of preparation of the compounded solution improves, but the stability of the hydrogel obtained deteriorates, and it is not preferable. Conversely, when the degree of saponification is too large, the solubility of the polyvinyl alcohol extremely decreases and it becomes difficult to prepare the compounded solution, and therefore the degree of saponification is preferably in the range of 80 to 98%, and more preferably 88 to 98%, but it is not limited to these ranges.

When the polyvinyl alcohol is contained in the layer A, the content of the polyvinyl alcohol with respect to the total amount of the hydrogel constituting the layer A is not particularly limited as long as the storage elastic modulus of the layer A can be within the range of 12,000 to 40,000 Pa. When the content is too small, improvement in the mechanical strength of the layer A cannot be expected. Conversely, when the content is too large, the polyvinyl alcohol cannot be completely dissolved in the gel, and precipitation and generation of undissolved polyvinyl alcohol develop, and a uniform gel body cannot be obtained. Therefore, the content is appropriately determined in view of balancing these aspects. Specifically, it is preferably 0.15 to 5% by weight with respect to the total amount of the hydrogel.

Moreover, the layer A 10 and the layer B 20 can contain an electrolyte depending on the needs, thereby it is possible to impart electric conductivity to the gel material constituting the layer A 10 and the layer B 20. When the gel sheet 1 is used as a bioelectrode, it is preferable that the alternating current impedance of each of the layer A 10 and the layer B 20 at 10 Hz be 1,000Ω or less.

When imparting electric conductivity to the gel material, the content of the electrolyte in the gel material is preferably 0.05 to 10% by weight, and more preferably 2 to 6% by weight, with respect to the total amount of the layer A or the layer B. When the content of the electrolyte is too small, the impedance becomes high and the electric conductivity cannot be said to be good. Moreover, although the impedance decreases as the content of the electrolyte increases, when the content of the electrolyte is too large, the amount of water required to dissolve the electrolyte increases, which is not preferable.

The electrolyte is not particularly limited, and examples thereof include alkali metal halides such as sodium halide (for example, sodium chloride), lithium halide and potassium halide; alkali earth metal halides such as magnesium halide and calcium halide; and other metal halides. Moreover, as the electrolyte, hypochlorite, chlorite, chlorate, perchlorate, sulfate, carbonate, nitrate and phosphate of various metals are also preferably used. Moreover, as the electrolyte, inorganic salts such as an ammonium salt and various complex salts; salts of monovalent organic carboxylic acids such as acetic acid, benzoic acid and lactic acid; salts of polyvalent organic carboxylic acids such as tartaric acid; monovalent or divalent or higher valent salts of polyvalent carboxylic acids such as phthalic acid, succinic acid, adipic acid, citric acid; metal salts of organic acids such as sulfonic acid and amino acid; organic ammonium salts and the like are also preferable.

Moreover, to the layer A 10 and the layer B 20, a base such as sodium hydroxide may be appropriately added for the purpose of adjusting the pH.

Moreover, in order to make the layer B 20 follow up the electrode element, the layer B 20 may be made to be fixed more firmly. Specifically, a hydrophilic polymer or a water-insoluble polymer having adhesion can be contained as a tackifier. For example, as the hydrophilic polymer, polyacrylic acid or a salt thereof can be used. The amount of the polyacrylic acid or the salt thereof to be added is not particularly limited, but is preferably in the range of 0.25 to 2% by weight with respect to the total amount of the layer B. When the amount to be added is small, there is no effect of imparting adhesion, and when the amount to be added is large, adhesion does not become large in proportion to the amount to be added, and therefore it is desirable to set the amount to be added in view of balancing the whole.

Moreover, as the water-insoluble polymer having adhesion, hydrophobic monomers such as (meth)acrylate ester, vinyl acetate, maleate ester, rosin-based resin and the like may be added.

In particular, examples of the water-insoluble polymer having adhesion include any one of hydrophobic monomers such as (meth)acrylate ester, vinyl acetate, maleate ester and the like alone or a polymer of more than one thereof. Specifically, examples include a homopolymer or a plurality of copolymers of any of the hydrophobic monomers such as isooctyl (meth)acrylate, 2-ethylhexyl (meth)acrylate, butyl (meth)acrylate, vinyl acetate, dioctyl maleate. In addition to the monomers mentioned above, one or more of any of the hydrophobic monomers such as ethylene, propylene, butylene, methyl (meth)acrylate, ethyl (meth)acrylate may be further copolymerized. Further, silicone adhesives and natural rubber-based and synthetic rubber-based adhesives can also be contained. Among these, an acrylate ester copolymer is excellent in various properties and has high adhesion, and therefore is preferably used.

In order to disperse the water-insoluble polymer having adhesion in the layer B, it is preferable to use an emulsion where the polymer is emulsified and dispersed. Usually, the content of solids in the emulsion is 30 to 60% by weight and most of the balance is water.

For example, as an emulsion of an acrylate ester-based copolymer resin, trade name "Polysol PSA SE-1730" manufactured by Showa Denko KK, trade name "Vinyblan ADH-1048" manufactured by Nissin Chemical Industry Co., Ltd. and the like are preferably used.

The content of the water-insoluble polymer having adhesion in the layer B 20 may be adjusted according to the performance expected of the final product, but in order to obtain good adhesion to the electrode element, it is necessary to add 3% by weight or more with respect to the total amount of the layer B. The content is preferably 5% by weight or more, more preferably 8% by weight or more, particularly preferably 10% by weight or more. Moreover, since the water-insoluble polymer independently has a function as an adhesive, the content may be large. However, when the content is too large, the adhesive force does not improve by a certain value or more. Moreover, when the water-insoluble polymer is used as a hydrogel for a medical electrode, the electric conductivity of the gel also decreases, and therefore it is preferable to set the content to 20% by weight or less with respect to the total amount of the layer B in view of balancing these aspects. The content is more preferably 15% by weight or less, and particularly preferably 13% by weight or less.

Further, it is possible to add polyvinyl alcohol to the layer B 20 as a dispersion stabilizer depending on one's needs. Thereby, the adhesive force of the layer B can be further improved. Since the polyvinyl alcohol added to the layer B is for ensuring dispersion stability, the degree of saponification is preferably within the range of 50 to 75%.

The content of the polyvinyl alcohol in the layer B 20 is appropriately determined from the perspective of ensuring dispersion stability. The content is preferably 0.05 to 5% by weight.

Further, the layer A 10 and the layer B 20 may also contain other additives depending on one's needs. Examples of other additives include, for example, rust inhibitors, antifungal agents, antioxidants, defoaming agents, stabilizers, surfactants, colorants and the like.

The layer A 10 and the layer B 20 can be obtained by dissolving or homogeneously dispersing each of the materials mentioned above, a polymerization initiator, a solvent and the like, and polymerizing and crosslinking by heating, ultraviolet irradiation or the like. The polymerization initiator may be a thermal polymerization initiator or a photopolymerization initiator. The amount of the polymerization initiator to be added is preferably 0.01% by weight or more with respect to 100% by weight of a compounded solution before gelling in order to thoroughly perform the polymerization reaction and reduce the residual monomers, and is preferably 1.0% by weight or less in order to prevent discoloration (yellowing) and odor due to the reaction residues of the polymerization initiator. The amount to be added is more preferably 0.05 to 0.5% by weight. Further, when polymerization is performed by ultraviolet irradiation, the amount of integrated irradiation of ultraviolet light varies depending on the content of the polymerization initiator and the like, but, for example, the amount is preferably in the range of 1,000 mJ/cm$^2$ to 10,000 mJ/cm$^2$, and more preferably in the range of 2,000 mJ/cm$^2$ to 10,000 mJ/cm$^2$.

As the photopolymerization initiator, those which are cleaved by ultraviolet light or visible light to generate radicals are preferable, which include α-hydroxyketone, α-aminoketone, benzyl methyl ketal, bisacylphosphine oxide, metallocene and the like. More specifically, the examples include 2-hydroxy-2-methyl-1-phenyl-propan-1-one (product name: DAROCUR 1173, manufactured by Ciba Specialty Chemicals Inc.), 1-hydroxy-cyclohexyl-phenyl-ketone (product name: Irgacure 184, manufactured by Ciba Specialty Chemicals Inc.), 1-[4-(2-hydroxyethoxy)-phenyl]-2-hydroxy-2-methyl-propan-1-one (product name: Irgacure 2959, manufactured by Ciba Specialty Chemicals Inc.), 2-methyl-1-[(methylthio)phenyl]-2-morpholinopropan-1-one (product name: Irgacure 907, manufactured by Ciba Specialty Chemicals Inc.), 2-benzyl-2-dimethylamino-1-(4-morpholinophenyl)-butan-1-one (product name: Irgacure 369, manufactured by Ciba Specialty Chemicals Inc.), 2-hydroxy-1-{4-[4-(2-hydroxy-2-methyl-propionyl)-benzyl]phenyl}-2-methyl-propan-1-one (product name: Irgacure 127, manufactured by Ciba Specialty Chemicals Inc.). These can be used independently or in combination.

When the thickness of the gel sheet 1 is too small, there is difficulty in handling, and therefore an appropriate thickness is selected in view of these aspects. The thickness is preferably in the range of 0.2 mm to 2.0 mm. In particular, the thickness is preferably 0.3 mm to 1.2 mm, and more preferably 0.5 mm to 1.0 mm.

Regarding the ratio of the thickness of the layer A 10 to that of the layer B 20 in the gel sheet 1, when the ratio of the layer A is too large, there is a possibility that the adhesion of the layer B to the electrode element may be inhibited. Conversely, when the ratio of the layer B increases, there is a concern that the gel will run off from the side. Therefore, the ratio is appropriately determined in view of balancing these aspects. Specifically, the thickness ratio A/B of the layer A 10 to the layer B 20 is preferably 0.25 to 3.5.

Moreover, in the gel sheet 1, an intermediate base material may be embedded along the in-plane direction depending on one's needs, in order to reinforce the gel sheet and to improve the shape retaining property when cutting and the like. The intermediate base material can be embedded so as to be placed between the layer A 10 and the layer B 20. Alternatively, the intermediate base material may be embedded in either the layer A 10 or the layer B 20, and not between the layers.

As a specific aspect, the intermediate base material embedded in the gel sheet 1 can be constituted of a nonwoven fabric or a woven fabric. As the material of the nonwoven fabric and the woven fabric, natural fibers of cellulose, silk, hemp and the like, synthetic fibers of polyester, nylon, rayon, polyethylene, polypropylene, polyurethane and the like, or mixed fibers thereof can be used. A binder may be used depending on one's needs, and further, the material may be colored depending on one's needs.

The method for producing the nonwoven fabric is not particularly limited, but examples thereof include a dry method, wet method, spunbond method, melt blown method, airlaid method, chemical bond method, thermal bond method, needle punching method, and a water-flow interlacing method. To control the position of the intermediate base material, it is preferable to adopt a production method in accordance with weight per unit area and material to have an even weight per unit area. As for the woven fabric as well, the production method is not particularly limited, and can be appropriately selected from, for example, plain weaving, tricot, raschel and the like.

Moreover, the weight per unit area of the woven or nonwoven fabric is not particularly limited as long as it is a weight per unit area capable of obtaining predetermined physical properties as an intermediate base material, but is preferably 10 to 40 g/m$^2$, and more preferably 10 to 28 g/m$^2$. When the weight per unit area of the woven or nonwoven fabric is too small, the gel sheet cannot be reinforced or the like, and unevenness of the weight per unit area becomes large, so that the permeability of liquid at the time of producing the gel sheet varies depending on positions, and there would be a possibility that the position of the intermediate base material fluctuate. Moreover, when the weight per unit area is too large, the intermediate base material becomes hard, and there would be a possibility that the following property to the skin and the like of the gel sheet 1 may be impaired and that the penetration property may be adversely affected. Therefore, the weight per unit area is appropriately determined in view of balancing these aspects.

Moreover, a semipermeable membrane may be used as a material for the intermediate base material. This semipermeable membrane is constituted of cellophane, cellulose acetate and the like, and it is difficult to pass water and a moisturizing agent as compared to a woven fabric or a nonwoven fabric, so that the compositions of each of the layer A and the layer B at the time of production can be retained for a longer period of time.

When the thickness of the intermediate base material is too large, the permeability of liquid degenerates and there would be cases where the penetration property is adversely affected. Conversely, when the thickness is too small, there would be a possibility that reinforcement and the like of the gel sheet cannot be achieved, or that the position of the intermediate base material fluctuates, similarly to the case where the weight per unit area is too small. Therefore, the thickness of the intermediate base material is appropriately determined in view of these aspects. The thickness of the intermediate base material is preferably in the range of 0.02 mm to 2.0 mm. Moreover, the thickness is more preferably 0.02 mm to 0.5 mm, and particularly preferably 0.03 to 0.3 mm.

As a method for producing the gel sheet 1, detailed conditions differ depending on the compositions of the layer A 10 and the layer B 20, the material and thickness of the intermediate base material and the like, and it is not particularly limited. For example, in the case of embedding the intermediate base material, it is possible to appropriately adopt a method of holding the intermediate base material in the air in a state in which tension of a certain magnitude or more is applied to the intermediate base material, pouring a monomer compounded solution onto the upper surface and the lower surface of the intermediate base material, and thus forming a sheet by polymerization by light irradiation or the like, a method of preparing gel materials of a sheet-like layer A and layer B both having a smooth surface, respectively, placing the intermediate base material held in a state in which tension of a certain magnitude or more is applied thereto between the gel materials, followed by conjugation, a method of preparing a sheet-like A layer having a smooth surface, mounting the intermediate base material onto the layer A in a state in which tension of a certain magnitude or more is applied thereto depending on one's needs, pouring a monomer compounded solution of a layer B onto the intermediate base material, and further conducting polymerization by light irradiation or the like, and the like.

Moreover, it is also possible to provide a gel sheet in a roll state, and sequentially conduct the production process mentioned above.

Depending on one's needs, it is possible to provide a base film on one side of the gel sheet 1, and to provide a top film on the side opposite to the side provided with the base film.

As the base film, for example, a resin film made of resin such as polyester, polyolefin, polystyrene, polyurethane and the like; paper; paper laminated with the resin film; and the like can be used.

It is preferable that the surface of the base film contacting the gel sheet 1 be subjected to release treatment. Examples of the method of release treatment include silicone coating and the like, and in particular, baking-type silicone coating which involves crosslinking and hardening reactions by heat or ultraviolet light is preferable. As a film to be subjected to release treatment, a biaxially stretched PET (polyethylene terephthalate) film, an OPP (stretched polypropylene) film and the like are particularly preferable.

Regarding the top film, it is basically possible to use the same material as that for the base film, but in the case where, in a state where the top film is provided, polymerization is conducted by ultraviolet irradiation thereon, it is preferable to select a film of a material that does not block light so as not to prevent photopolymerization.

The gel sheet as described above can be used by attaching the surface of the layer A 10 to the skin as a bioelectrode in electroencephalography and the like. In this case, the side of the layer B 20 is made to an electrode element by removing the top film, and closely attaching a body having an electrically conductive layer formed by print-coating an electrically conductive ink containing metal such as Ag, Ag/AgCl or the like and carbon or the like on a resin film, or a body having an electrically conductive layer formed by laminating an electrically conductive film where metal foil (aluminum, stainless steel, Ag or the like) or carbon or the like is kneaded on the resin film. Since the storage elastic modulus of the layer B 20 is 2,000 to 10,000 Pa, the layer B 20 is softer than the Layer A 10, and therefore the following property to the electrode element is good and air bubbles do not develop between the layer B 20 and the electrode element.

EXAMPLES

Hereinafter, the present invention shall be described in more detail based on Examples and Comparative Examples, but the present invention is not limited to these Examples.

Example 1

Composition of Layer A

With respect to the total amount of a layer A, 24% by weight of acrylamide as a monofunctional monomer, 0.036% by weight of N,N'-methylenebisacrylamide, 5% by weight of sodium chloride, and 40.9% by weight of glycerin as crosslinking monomers were weighed, and to this mixture solution were added 3% by weight of polyvinyl alcohol (having degree of saponification of 88%) and 0.1% by weight of 2-hydroxy-2-methyl-1-phenyl-propan-1-one (trade name: Irgacure IR1173) as a photopolymerization initiator, and further 1% by weight each of citric acid 3Na and citric acid as pH buffer agents, and finally ion-exchange water was added to make the total 100% by weight, and a monomer compounded solution of the layer A was obtained.

Composition of Layer B

With respect to the total amount of a layer B, 20% by weight of acrylamide as a monofunctional monomer, and 0.032% by weight of N,N'-methylenebisacrylamide, 5% by weight of sodium chloride, and 44.9% by weight of glycerin as crosslinking monomers were weighed, and to this mixture solution were added 0.1% by weight of 2-hydroxy-2-methyl-1-phenyl-propan-1-one (trade name: Irgacure IR1173) as a photopolymerization initiator, and further 1% by weight each of citric acid 3Na and citric acid as pH buffer agents, and finally ion-exchange water was added to make the total 100% by weight, and a monomer compounded solution of the layer B was obtained.

Production of Gel Sheet

The resulting monomer compounded solution of the layer B was dripped onto a silicone-coated PET film and by allowing to pass through a certain clearance, the liquid was uniformly spread out and was fixed so as to have a thickness of 0.6 mm. The liquid was irradiated with ultraviolet light having an energy amount of 500 mJ/cm$^2$ using a metal halide lamp to obtain the layer B having a thickness of 0.6 mm. The monomer compounded solution of the layer A was dropped on the obtained layer B, and a similarly silicone-coated PET film was covered from above, and the liquid was uniformly spread out and was fixed so as to have a thickness of 0.3 mm. The liquid was irradiated with infrared light having an energy amount of 3,000 mJ/cm$^2$ using a metal halide lamp to obtain a gel sheet having a thickness of 0.9 mm. The thickness of the gel sheet was measured by peeling off the PET film attached on both the sides using a micrometer.

Example 2

A gel sheet was prepared in the same manner as that in Example 1 mentioned above, except that the thicknesses of the layer A and that of the layer B were 0.6 mm and 0.3 mm, respectively.

Example 3

A gel sheet was prepared in the same manner as that in Example 2 mentioned above, except that the content of polyvinyl alcohol in the layer A was 2% by weight and the content of glycerin was 41.9% by weight.

Example 4

In Example 1 mentioned above, the monomer compounded solution of the layer B was changed as follows.

That is, with respect to the total amount of the layer B, 18% by weight of acrylamide as a monofunctional monomer, and 0.030% by weight of N,N'-methylenebisacrylamide, 2% by weight of sodium chloride, and 39.9% by weight of glycerin as crosslinking monomers were weighed, and to this mixture solution were added 0.1% by weight of 2-hydroxy-2-methyl-1-phenyl-propan-1-one (trade name: Irgacure IR1173) as a photopolymerization initiator, and further 1% by weight each of citric acid 3Na and citric acid as pH buffer agents, and finally 21.8% by weight (10.9% by weight of solid content, and 10.9% by weight of water) of an emulsion of an acrylate ester-based copolymer (50% by weight of solid content, trade name "Polysol PSA SE-1730", manufactured by Showa Highpolymer Co., Ltd.) as a water-insoluble polymer and 0.2% by weight of polyvinyl alcohol, with a degree of saponification of 65%, which is an amphiphilic polymer as a dispersion stabilizer. The mixture solution was stirred for several minutes until the solution was homogeneous, and a milky white compounded solution was obtained. To the mixture solution was added 16% by weight of ion-exchange water to make the total 100% by weight, and a monomer compounded solution of the layer B was obtained.

A gel sheet was prepared in the same manner as that in Example 1, except that the monomer compounded solution mentioned above was used as the layer B.

Example 5

A gel sheet was prepared in the same manner as that in Example 4 mentioned above, except that the thicknesses of the layer A and that of the layer B were 0.6 mm and 0.3 mm, respectively.

Example 6

A gel sheet was prepared in the same manner as that in Example 5 mentioned above, except that a nylon mesh serving as an intermediate base material was embedded between the layer A and the layer B in the production process of the gel sheet.

Example 7

A gel sheet was prepared in the same manner as that in Example 2 mentioned above, except that a nylon mesh serving as an intermediate base material was embedded between the layer A and the layer B in the production process of the gel sheet.

Example 8

A gel sheet was prepared in the same manner as that in Example 7 mentioned above, except that in the monomer compounded solution of the layer B of Example 7 mentioned above, 5% by weight of polyacrylic acid Na (an aqueous solution of 20% by weight of solid content, trade name "JURYMER AC-20H", manufactured by Toagosei Co., Ltd.) was additionally dissolved as a tackifier, the content of acrylamide as a monofunctional monomer was 19% by weight, and the content of water was 24% by weight.

Example 9

A gel sheet was prepared in the same manner as in Example 8 mentioned above, except that the compositions of the monomer compounded solutions of the layer A and the layer B in Example 8 mentioned above were changed as shown in Table 2 and that the intermediate base material was not embedded.

Example 10

A gel sheet was prepared in the same manner as that in Example 8 mentioned above, except that the compositions of the monomer compounded solutions of the layer A and the layer B were changed as shown in Table 2.

Comparative Example 1

A gel sheet was constituted of a layer B simple substance (having a thickness of 0.9 mm) not containing polyvinyl alcohol in Example 1, without forming a laminate structure.

Comparative Example 2

A gel sheet was prepared in the same manner as that in Example 2 mentioned above, except that, in the layer A, polyvinyl alcohol was not contained, the content of acrylamide as a monofunctional monomer was reduced to 20% by weight, the content of N,N'-methylenebisacrylamide as a crosslinking monomer was increased to 0.5% by weight, the content of water was 28% by weight, and the content of glycerin was 44.4% by weight.

Comparative Example 3

A gel sheet was prepared in the same manner as that in Example 2 mentioned above, except that an electrically conductive rubber having a thickness of 2 mm (a semiconductive gel (having an Asker C hardness of 15) made of urethane resin, and manufactured by Exseal Co., Ltd.) was used as the layer A.

Comparative Example 4

A gel sheet was constituted of a layer A simple substance (having a thickness of 0.9 mm) in Example 1, without forming a laminate structure.

The compositions of the gel sheets obtained in Examples 1 to 10 and Comparative Examples 1 to 4 are collectively shown in Tables 1 and 2.

TABLE 1

| | | | Example | | | |
|---|---|---|---|---|---|---|
| | | | 1 | 2 | 3 | 4 |
| Layer A (Skin side) | Water | Ion-exchange water | 25 | 25 | 25 | 25 |
| | Water-soluble synthetic polymer | Polyvinyl alcohol (Degree of saponification of 88%) | 3 | 3 | 2 | 3 |
| | Polyhydric alcohol (Moisturizing agent) | Glycerin | 40.9 | 40.9 | 41.9 | 40.9 |
| | Polymer matrix | Monofunctional monomer  Acrylamide | 24 | 24 | 24 | 24 |
| | | Crosslinkable monomer  N,N'-methylenebisacrylamide | 0.036 | 0.036 | 0.036 | 0.036 |
| | Electrolyte salt | Sodium chloride | 5 | 5 | 5 | 5 |
| | pH buffer agent | Citric acid | 1 | 1 | 1 | 1 |
| | | Citric acid salt | 1 | 1 | 1 | 1 |
| | Other additive | Photopolymerization initiator IR1173 | 0.1 | 0.1 | 0.1 | 0.1 |
| | Thickness of layer A (mm) | | 0.3 | 0.6 | 0.6 | 0.3 |

TABLE 1-continued

| | | | | | | |
|---|---|---|---|---|---|---|
| Layer between layer A and layer B | Presence or absence of intermediate base material | | Absent | Absent | Absent | Absent |
| Layer B (Element side) | Water | Ion-exchange water | 28 | 28 | 28 | 16 |
| | Water-soluble synthetic polymer | Polyvinyl alcohol (Degree of saponification of 88%) | — | — | — | — |
| | Polyhydric alcohol (Moisturizing agent) | Glycerin | 44.9 | 44.9 | 44.9 | 39.9 |
| | Polymer matrix | Monofunctional monomer  Acrylamide | 20 | 20 | 20 | 18 |
| | | Crosslinkable monomer  N,N'-methylenebisacrylamide | 0.032 | 0.032 | 0.032 | 0.030 |
| | Electrolyte salt | Sodium chloride | 5 | 5 | 5 | 2 |
| | pH buffer agent | Citric acid | 1 | 1 | 1 | 1 |
| | | Citric acid salt | 1 | 1 | 1 | 1 |
| | Other additive | Photopolymerization initiator IR1173 | 0.1 | 0.1 | 0.1 | 0.1 |
| | | Tackifier (Polyacrylic acid Na) | — | — | — | — |
| | | Tackifier (Acrylic acid ester copolymer) + Polyvinyl alcohol (Degree of saponification of 65%) | — | — | — | 22 |
| | Thickness of layer B (mm) | | 0.6 | 0.3 | 0.3 | 0.6 |

| | | | Example | | |
|---|---|---|---|---|---|
| | | | 5 | 6 | 7 |
| Layer A (Skin side) | Water | Ion-exchange water | 25 | 25 | 25 |
| | Water-soluble synthetic polymer | Polyvinyl alcohol (Degree of saponification of 88%) | 3 | 3 | 3 |
| | Polyhydric alcohol (Moisturizing agent) | Glycerin | 40.9 | 40.9 | 40.9 |
| | Polymer matrix | Monofunctional monomer  Acrylamide | 24 | 24 | 24 |
| | | Crosslinkable monomer  N,N'-methylenebisacrylamide | 0.036 | 0.036 | 0.036 |
| | Electrolyte salt | Sodium chloride | 5 | 5 | 5 |
| | pH buffer agent | Citric acid | 1 | 1 | 1 |
| | | Citric acid salt | 1 | 1 | 1 |
| | Other additive | Photopolymerization initiator IR1173 | 0.1 | 0.1 | 0.1 |
| | Thickness of layer A (mm) | | 0.6 | 0.6 | 0.6 |
| Layer between layer A and layer B | Presence or absence of intermediate base material | | Absent | Present | Present |
| Layer B (Element side) | Water | Ion-exchange water | 16 | 16 | 28 |
| | Water-soluble synthetic polymer | Polyvinyl alcohol (Degree of saponification of 88%) | — | — | — |
| | Polyhydric alcohol (Moisturizing agent) | Glycerin | 39.9 | 39.9 | 44.9 |
| | Polymer matrix | Monofunctional monomer  Acrylamide | 18 | 18 | 20 |
| | | Crosslinkable monomer  N,N'-methylenebisacrylamide | 0.030 | 0.030 | 0.032 |
| | Electrolyte salt | Sodium chloride | 2 | 2 | 5 |
| | pH buffer agent | Citric acid | 1 | 1 | 1 |
| | | Citric acid salt | 1 | 1 | 1 |
| | Other additive | Photopolymerization initiator IR1173 | 0.1 | 0.1 | 0.1 |
| | | Tackifier (Polyacrylic acid Na) | — | — | — |
| | | Tackifier (Acrylic acid ester copolymer) + Polyvinyl alcohol (Degree of saponification of 65%) | 22 | 22 | — |
| | Thickness of layer B (mm) | | 0.3 | 0.3 | 0.3 |

TABLE 2

| | | | Example | | | Comparative Example |
|---|---|---|---|---|---|---|
| | | | 8 | 9 | 10 | 1 |
| Layer A (Skin side) | Water | Ion-exchange water | 25 | 21 | 21 | 28 |
| | Water-solable synthetic polymer | Polyvinyl alcohol (Degree of saponification of 88%) | 3 | 3 | 3 | — |
| | Polyhydric alcohol (Moisturizing agent) | Glycerin | 40.9 | 44.9 | 44.9 | 44.9 |
| | Polymer matrix | Monofunctional monomer  Acrylamide | 24 | 24 | 24 | 20 |
| | | Crosslinkable monomer  N,N'-methylenebisacrylamide | 0.036 | 0.036 | 0 036 | 0.032 |
| | Electrolyte salt | Sodium chloride | 5 | 5 | 5 | 5 |
| | pH buffer agent | Citric acid | 1 | 1 | 1 | 1 |
| | | Citric acid salt | 1 | 1 | 1 | 1 |
| | Other additive | Photopolymerization initiator IR1173 | 0.1 | 0.1 | 0.1 | 0.1 |
| | Thickness of layer A (mm) | | 0.6 | 0.6 | 0.6 | 0.9 |

TABLE 2-continued

| | | | | | | |
|---|---|---|---|---|---|---|
| Layer between layer A and layer B | Presence or absence of intermediate base material | | | Present | Absent | Present | Absent |
| Layer B (Element side) | Water | Ion-exchange water | | 24 | 22 | 22 |
| | Water-solable synthetic polymer | Polyvinyl alcohol (Degree of saponification of 88%) | | — | — | — |
| | Polyhydric alcohol (Moisturizing agent) | Glycerin | | 44.9 | 50.4 | 50.4 |
| | Polymer matrix | Monofunctional monomer | Acrylamide | 19 | 20 | 20 |
| | | Crosslinkable monomer | N,N'-methylenebisacrylamide | 0.032 | 0.036 | 0.036 |
| | Electrolyte salt | Sodium chloride | | 5 | 2 | 2 |
| | pH buffer agent | Citric acid | | 1 | 1 | 1 |
| | | Citric acid salt | | 1 | 1 | 1 |
| | Other additive | Photopolymerization initiator IR1173 | | 0.1 | 0.1 | 0.1 |
| | | Tackifier (Polyacrylic acid Na) | | 5 | 3.5 | 3.5 |
| | | Tackifier (Acrylic acid ester copolymer) + Polyvinyl alcohol (Degree of saponification of 65%) | | — | — | — |
| Thickness of layer B (mm) | | | | 0.3 | 0.3 | 0.3 |

| | | | | Comparative Example | | |
|---|---|---|---|---|---|---|
| | | | | 2 | 3 | 4 |
| Layer A (Skin side) | Water | Ion-exchange water | | 28 | Electrically conductive rubber | 25 |
| | Water-solable synthetic polymer | Polyvinyl alcohol (Degree of saponification of 88%) | | — | | 3 |
| | Polyhydric alcohol (Moisturizing agent) | Glycerin | | 44.4 | | 40.9 |
| | Polymer matrix | Monofunctional monomer | Acrylamide | 20 | | 24 |
| | | Crosslinkable monomer | N,N'-methylenebisacrylamide | 0.5 | | 0.036 |
| | Electrolyte salt | Sodium chloride | | 5 | | 5 |
| | pH buffer agent | Citric acid | | 1 | | 1 |
| | | Citric acid salt | | 1 | | 1 |
| | Other additive | Photopolymerization initiator IR1173 | | 0.1 | | 0.1 |
| | Thickness of layer A (mm) | | | 0.6 | 2 | 0.9 |
| Layer between layer A and layer B | Presence or absence of intermediate base material | | | Absent | Absent | Absent |
| Layer B (Element side) | Water | Ion-exchange water | | 28 | 28 | |
| | Water-solable synthetic polymer | Polyvinyl alcohol (Degree of saponification of 88%) | | — | — | |
| | Polyhydric alcohol (Moisturizing agent) | Glycerin | | 44.9 | 44.9 | |
| | Polymer matrix | Monofunctional monomer | Acrylamide | 20 | 20 | |
| | | Crosslinkable monomer | N,N'-methylenebisacrylamide | 0.032 | 0.032 | |
| | Electrolyte salt | Sodium chloride | | 5 | 5 | |
| | pH buffer agent | Citric acid | | 1 | 1 | |
| | | Citric acid salt | | 1 | 1 | |
| | Other additive | Photopolymerization initiator IR1173 | | 0.1 | 0.1 | |
| | | Tackifier (Polyacrylic acid Na) | | | | |
| | | Tackifier (Acrylic acid ester copolymer) + Polyvinyl alcohol (Degree of saponification of 65%) | | | | |
| | Thickness of layer B (mm) | | | 0.3 | 0.3 | |

(Evaluation of Gel Sheets)

Various tests were conducted on the gel sheets obtained in Examples 1 to 10 and Comparative Examples 1 to 4.

Measurements of Adhesive Force of Gel Sheets

In accordance with JIS Z0237: 2009, test pieces were prepared by culling each gel sheet into 120 mm×20 mm, attaching a Bakelite plate on a gel surface (the layer A or the layer B) that appeared after peeling off the PET film, and rolling a pressure roller of 2 kg back and forth once to pressure bond the Bakelite plate. A rheometer (CR-500 DX, manufactured by Sun Scientific Co., Ltd.) was used for measurements, under the measuring conditions of angle of 90° and speed of 300 mm/min. Stress values (N/20 mm) at points from the starting point of measurement to predetermined peeling points (30, 40, 50, 60, and 70 mm) were measured, and the average value of 3 tests (total of 15 points) was taken as the adhesive force. The measurements were carried out in a measuring environment of a temperature of 23±5° C. and humidity of 55%±10%. The results of the measurements are shown in Tables 3 and 4.

Measurements of Adhesive Force of Gel Sheets (Evaluation of Feeling when Used)

The gel sheet was cut into 40 mm squares and the surface of the layer A was pressed against the scalp for 1 minute. Thereafter, the gel sheet was peeled off by hand to evaluate the degree of clinging of the hair. Signs of G (Good): when there is no pain, F (Fair): when there is no pain, but when gel adheres to the hair or when the hair is pulled, and P (Poor): when the hair falls out are used. The measurements were carried out in a measuring environment of a temperature of 23±5° C. and humidity of 55%±10%. The results of the measurements are shown in Tables 3 and 4.

Viscoelastic Properties of Gel Sheets

The storage elastic modulus, loss elastic modulus, and loss tangent (tan θ) of each of the layer A and the layer B of the gel sheets were measured. Specifically, viscoelasticity of a strain amount of 1% was measured at a temperature of 23° C. and a frequency of 10 Hz using a viscoelasticity measuring device (MR-102, manufactured by Anton Paar GmbH). A gel piece of 25φ was attached to a parallel plate of 25ϕ made of SUS, and a jig was pressed on the gel piece until the load point of 1 N, then the storage elastic modulus and the loss elastic modulus at 10 Hz were measured and the loss tangent (tan θ) was calculated from the values. The results of the measurements are shown in Tables 3 and 4. The higher the storage elastic modulus is, the more it shows elasticity, and therefore it can be used as an index of hardness.

Measurements of Hardness of Gel Sheets

Young's modulus of the gel sheet was measured by pressing a 12ϕ column made of SUS under the conditions of a temperature of 23±5° C. humidity of 55±10% and a test speed of 0.1 mm/min using a Tensilon Universal Testing Machine (RTE-1210 manufactured by Orientec Co., Ltd.). An S-S curve up to 2.98 N was measured under the conditions mentioned above. The test piece of the gel sheet was 25 mm×40 mm, and a sufficient area was secured for the 12ϕ column.

The Young's modulus was calculated from the S-S curve from a stress of about 2.0 N to about 2.5 N using the following mathematical formula.

Young's modulus=difference in stress value between two points/cross-sectional area×(thickness of gel sheet−time when 2.0 N×displacement per time)/strain amount (deformation amount from 2.0 N to 2.5 N)

Measurements of Shore Hardness of Gel Sheets

Asker C hardness of the surfaces of the layer A and the layer B of the gel sheet was measured in accordance with JIS K 7312. The results of the measurements are shown in Tables 3 and 4. As shown in Tables 3 and 4, the Asker C hardness of the surface of the layer A was 9 to 42, and the surface was dented by a convex portion pressed at the time of measurement, but it was restored. Moreover, the Asker C hardness of the surface of the layer B was 0, and the surface was scratched by a pressed convex portion.

Measurements of Stress Relaxation Force of Gel Sheets

A 12ϕ column made of SUS was pressed under the conditions of a temperature of 23±5° C., humidity of 55±10% and a test speed of 0.1 mm/min using a Tensilon Universal Testing Machine (RTE-1210 manufactured by Orientec Co., Ltd.). After applying a displacement until reaching 40 N, the displacement was fixed at 40 N and was kept for 40 sec. The stress relaxation value at the time was measured. The obtained value was divided by 40 N to show in terms of ratio how much stress value decreased with respect to the applied stress.

Electric Performance Evaluation of Gel Sheets

First, the gel sheets were separated into the layer As and the layer Bs. Then, the layer As and the layer Bs were each cut into 20 mm squares, and the resulting A layers or B layers were overlapped with each other to prepare test pieces. The test pieces were placed between SUS plates, and the alternating current impedance (Ω) of each of the layer A and the layer B was measured under the conditions of a storage oscilloscope (an input voltage of 10 V, frequency of 10 Hz, resistance of 1 MΩ). The results of the measurements are shown in Tables 3 and 4.

TABLE 3

| | | Example | | | | | | |
|---|---|---|---|---|---|---|---|---|
| | | 1 | 2 | 3 | 4 | 5 | 6 | 7 |
| Adhesive force (N/20 mm) | Layer A | 1.1 | 0.8 | 1.4 | 1.1 | 1.1 | 1.1 | 1.1 |
| | Layer B | 5.4 | 4.7 | 4.3 | 11 | 10.6 | 10.8 | 4.2 |
| Adhesive force (Feeling when used) | Layer A | G | G | F | G | G | G | G |
| Storage elastic modulus (Pa) | Layer A | 13012 | 22899 | 15260 | 14562 | 23451 | 22961 | 23113 |
| | Layer B | 7005 | 4139 | 4054 | 9188 | 8582 | 8425 | 4352 |
| AC impedance (Ω) | Layer A | 450 | 386 | 381 | 452 | 347 | 344 | 342 |
| | Layer B | 11.2 | 15.0 | 15.4 | 340 | 287 | 255 | 13.2 |
| Young's modulus (MPa) | Layer A | 0.46 | 0.33 | 0.28 | 0.46 | 0.33 | 0.33 | 0.33 |
| | Layer B | 0.25 | 0.25 | 0.25 | 0.26 | 0.26 | 0.26 | 0.25 |
| Asker C hardness | Layer A | 9 Without scratch | 9 Without scratch | 9 Without scratch | 9 Without scratch | 9 Without scratch | 9 Without scratch | 9 Without scratch |
| | Layer B | 0 With scratch | 0 With scratch | 0 With scratch | 0 With scratch | 0 With scratch | 0 With scratch | 0 With scratch |
| Stress relaxation (%) | Layer A | 37 | 37 | 45 | 37 | 37 | 37 | 37 |
| | Layer B | 50 | 50 | 50 | 47 | 47 | 47 | 50 |

TABLE 4

| | | Example | | | Comparative Example | | | |
|---|---|---|---|---|---|---|---|---|
| | | 8 | 9 | 10 | 1 | 2 | 3 | 4 |
| Adhesive force (N/20 mm) | Layer A | 1.1 | 1.2 | 1.2 | 6.2 | 0.3 | 0.2 | 1.4 |
| | Layer B | 7.2 | 3.8 | 3.6 | | 4.2 | 3.8 | |
| Adhesive force (Feeling when used) | Layer A | G | G | G | P | *1 | G | G |
| Storage elastic modulus (Pa) | Layer A | 23094 | 23511 | 23651 | 9850 | *1 | 56666 | 31520 |
| | Layer B | 3874 | 8074 | 8182 | | 3878 | 4112 | |
| AC impedance (Ω) | Layer A | 355 | 410 | 408 | 32 | 240 | *2 | 520 |
| | Layer B | 12.2 | 352 | 381 | | 150 | 150 | |

TABLE 4-continued

|  |  | Example | | | Comparative Example | | | |
| --- | --- | --- | --- | --- | --- | --- | --- | --- |
|  |  | 8 | 9 | 10 | 1 | 2 | 3 | 4 |
| Young's modulus (MPa) | Layer A | 0.33 | 0.33 | 0.33 | 0.25 | 1.52 | 0.43 | 0.5 |
|  | Layer B | 0.25 | 0.25 | 0.25 |  | 0.25 | 0.25 |  |
| Asker C hardness | Layer A | 9 Without scratch | 9 Without scratch | 9 Without scratch | 0 With scratch | 42 With scratch | 15 Without scratch | 9 Without scratch |
|  | Layer B | 0 With scratch | 0 With scratch | 0 With scratch |  | 0 With scratch | 0 With scratch |  |
| Stress relaxation (%) | Layer A | 37 | 37 | 37 | 50 | *3 | 22 | 37 |
|  | Layer B | 50 | 48 | 48 |  | 50 | 50 |  |

*1 Handling of gel was bad and damaged.
*2 Over ranged
*3 Unmeasurable due to damage.

As shown in Tables 3 and 4, according to the present invention, gel sheets showing different behaviors in respective layers were obtained, and adequate physical properties were exhibited on the skin side and the electrode element side, respectively.

The gel sheets obtained in the Examples and the Comparative Examples were laminated on electrode elements obtained by laminating electrically conductive films where carbon has been kneaded on resin films. A gel sheet obtained in Comparative Example 4 was too hard, exhibited low adhesive force, and showed no following property to the electrode element and adhesion was poor.

REFERENCE SIGNS LIST

1 A gel sheet
10 Layer A
20 Layer B

All publications, patents and patent applications cited in this specification shall be incorporated herein by reference in their entirety.

The invention claimed is:

1. A gel sheet having a laminated structure of a layer A and a layer B, wherein a storage elastic modulus of the layer A at 23° C. and 10 Hz is 12,000 to 40,000 Pa, and a storage elastic modulus of the layer B at 23° C. and 10 Hz is 2,000 to 10,000 Pa;

wherein the layer A and the layer B are hydrogels comprising a polymer matrix, water and polyhydric alcohol, and the polymer matrix is a copolymer of one or more monofunctional monomers selected from a (meth)acrylamide-based monomer and a (meth)acrylate ester, and a crosslinkable monomer; and wherein the layer A further comprises polyvinyl alcohol in an amount of 0.15% to 5%.

2. The gel sheet according to claim 1, wherein an adhesive force of the layer A to a Bakelite plate is 0.1 to 2.0 N/20 mm, and an adhesive force of the layer B to the Bakelite plate is 2.5 to 15 N/20 mm.

3. The gel sheet according to claim 1, having a thickness of 0.2 mm to 2.0 mm.

4. The gel sheet according to claim 1, wherein a ratio of a thickness of the layer A to a thickness of the layer B (AB) is 0.25 to 3.5.

5. The gel sheet according to claim 1, wherein the crosslinkable monomer is in an amount of 0.01%-0.1% by weight with respect to a total amount of the hydrogels.

6. The gel sheet according to claim 1, wherein an alternating current impedance of the layer A and that of the layer B at 10 Hz are both 1,000Ω or less.

7. The gel sheet according to claim 1, being an adhesive gel sheet for skin to be used by attaching a surface of the layer A to the skin.

* * * * *